(12) United States Patent
Nock et al.

(10) Patent No.: US 8,532,747 B2
(45) Date of Patent: Sep. 10, 2013

(54) BIOPSY MARKER DELIVERY DEVICE

(75) Inventors: Andrew P. Nock, Centerville, OH (US); Ramon Ramos, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 861 days.

(21) Appl. No.: 12/196,301

(22) Filed: Aug. 22, 2008

(65) Prior Publication Data

US 2010/0049084 A1 Feb. 25, 2010

(51) Int. Cl.
*A61B 6/00* (2006.01)

(52) U.S. Cl.
USPC ............................ 600/431; 600/562; 606/116

(58) Field of Classification Search
USPC ................. 600/562–572, 431–435; 606/167, 606/170, 180, 116
See application file for complete search history.

(56) References Cited

U.S. PATENT DOCUMENTS

| | | | |
|---|---|---|---|
| 3,288,901 A | 11/1966 | Clark | |
| 4,210,478 A | 7/1980 | Shoney | |
| 4,921,483 A * | 5/1990 | Wijay et al. | 604/103.1 |
| 5,024,727 A | 6/1991 | Campbell et al. | |
| 5,192,301 A * | 3/1993 | Kamiya et al. | 606/213 |
| 5,429,597 A | 7/1995 | Demello et al. | |
| 5,526,822 A | 6/1996 | Burbank et al. | |
| 5,899,882 A | 5/1999 | Waksman et al. | |
| 6,086,544 A | 7/2000 | Hibner et al. | |
| 6,149,996 A | 11/2000 | Helgerson et al. | |
| 6,203,524 B1 * | 3/2001 | Burney et al. | 604/93.01 |
| 6,228,055 B1 | 5/2001 | Foerster et al. | |
| 6,347,241 B2 * | 2/2002 | Burbank et al. | 600/431 |
| 6,371,904 B1 | 4/2002 | Sirimanne et al. | |
| 6,626,849 B2 | 9/2003 | Huitema et al. | |
| 6,993,375 B2 | 1/2006 | Burbank et al. | |
| 6,994,712 B1 | 2/2006 | Fisher et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,229,417 B2 | 6/2007 | Foerster et al. | |
| 7,442,171 B2 | 10/2008 | Stephens et al. | |
| 7,465,279 B2 | 12/2008 | Beckman et al. | |
| 2004/0097981 A1 * | 5/2004 | Selis | 606/151 |
| 2005/0033272 A1 * | 2/2005 | Humayun | 606/4 |
| 2005/0096642 A1 * | 5/2005 | Appling et al. | 606/15 |
| 2005/0101967 A1 | 5/2005 | Weber et al. | |
| 2005/0277871 A1 * | 12/2005 | Selis | 604/60 |
| 2007/0010738 A1 | 1/2007 | Mark et al. | |
| 2007/0016017 A1 | 1/2007 | Mark et al. | |
| 2008/0195066 A1 | 8/2008 | Speeg et al. | |

FOREIGN PATENT DOCUMENTS

WO WO 2007/069105 6/2007

OTHER PUBLICATIONS

U.S. Appl. No. 60/869,736, filed Dec. 13, 2006, Ritchie et al.
U.S. Appl. No. 60/874,792, filed Dec. 13, 2006, Hibner et al.
European Search Report and Written Opinion dated Nov. 29, 2011 for Application No. EP09252037.

* cited by examiner

*Primary Examiner* — Rene Towa
(74) *Attorney, Agent, or Firm* — Frost Brown Todd LLC

(57) ABSTRACT

A biopsy device for delivering a biopsy marker to a biopsy site is disclosed. The biopsy device can include a marker deployer having a unitary endpiece disposed in a distal end of the cannula. The distal endpiece can be a molded component which includes a distal tip, a marker deployment ramp, and a marker engaging element that aids in retaining the marker in the cannula until the marker is meant to be deployed.

18 Claims, 5 Drawing Sheets

BIOPSY MARKER DELIVERY DEVICE

BACKGROUND

Biopsy samples have been obtained in a variety of ways in various medical procedures using a variety of devices. An exemplary biopsy device is the MAMMOTOME® brand device from Ethicon Endo-Surgery, Inc. of Cincinnati, Ohio. Biopsy devices may be used under stereotactic guidance, ultrasound guidance, MRI guidance, or otherwise.

Further exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Non-Provisional Patent Application Ser. No. 11/942,785, entitled "Revolving Tissue Sample Holder for Biopsy Device," filed Nov. 21, 2007. The disclosure of each of the above-cited U.S. Patents, U.S. Patent Application Publications, U.S. Provisional Patent Applications, and U.S. Non-Provisional Patent Application is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK®, MICROMARK®, and CORMARK® brand devices from Ethicon Endo-Surgery, Inc. of Cincinnati, Ohio. Further exemplary devices and methods for marking a biopsy site are disclosed in U.S. Pub. No. 2005/0228311, entitled "Marker Device and Method of Deploying a Cavity Marker Using a Surgical Biopsy Device," published Oct. 13, 2005; U.S. Pat. No. 6,996,433, entitled "Imageable Biopsy Site Marker," issued Feb. 7, 2006; U.S. Pat. No. 6,993,375, entitled "Tissue Site Markers for In Vivo Imaging," issued Jan. 31, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,044,957, entitled "Devices for Defining and Marking Tissue," issued May 16, 2006; U.S. Pat. No. 6,228,055, entitled "Devices for Marking and Defining Particular Locations in Body Tissue," issued May 8, 2001; and U.S. Pat. No. 6,371,904, entitled "Subcutaneous Cavity Marking Device and Method," issued Apr. 16, 2002. The disclosure of each of the above-cited U.S. Patents and U.S. Patent Application Publications is incorporated by reference herein.

It may be desirable to deploy markers from a cannula type deployer into the biopsy site. The marker should not unintentionally fall out of the deployer, and the force to deploy the marker should not be excessive.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
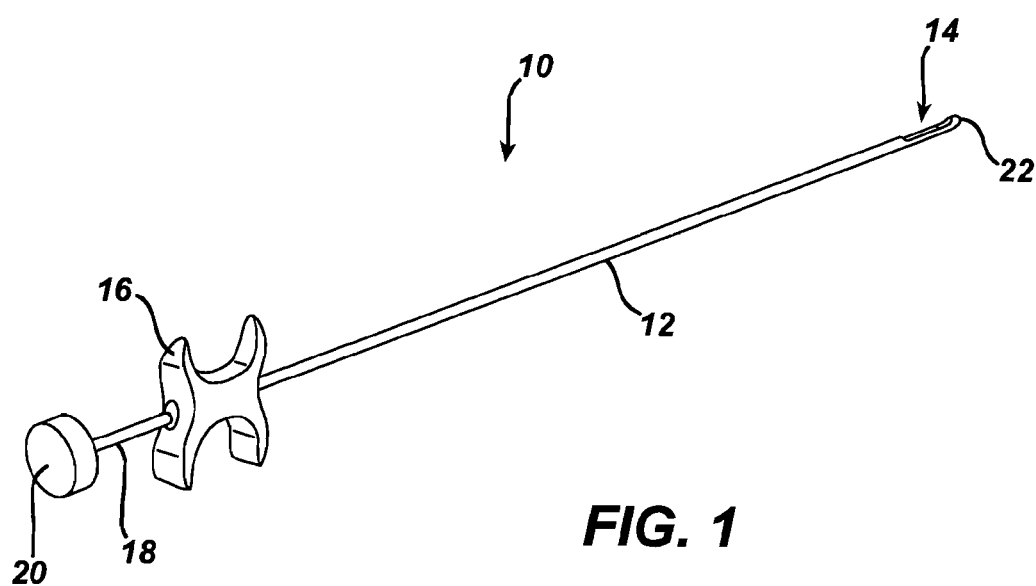
FIG. 1 depicts a perspective view of a marker delivery device.

FIG. 1 illustrates a marker delivery device 10 which includes an elongate outer cannula 12 having a marker exit, such as side opening 14 formed near to, but spaced proximally from, the distal end of the cannula 12.

A grip 16 can be provided at the proximal end of cannula 12. A push rod 18 can be provided, with push rod 18 extending coaxially in cannula 12 such that the push rod 18 is configured to translate within cannula 12 to displace one or more markers through the side opening 14 (see FIG. 2). Rod 18 can have sufficient rigidity in compression to push a marker from the internal lumen of cannula 12 out through opening 14, yet be relatively flexible in bending. A plunger 20 can be provided at the proximal end of rod 18 for forcing rod 18 distally in cannula 12 to deploy a marker out of the cannula 12.

A user may grasp grip 16 with two fingers, and may push on plunger 20 using the thumb on the same hand, so that the marker delivery device 10 can be operated by a user's single hand. A spring (not shown) or other feature may be provided about rod 18 to bias rod 18 proximally relative to grip 16 and cannula 12.

Figure 2:
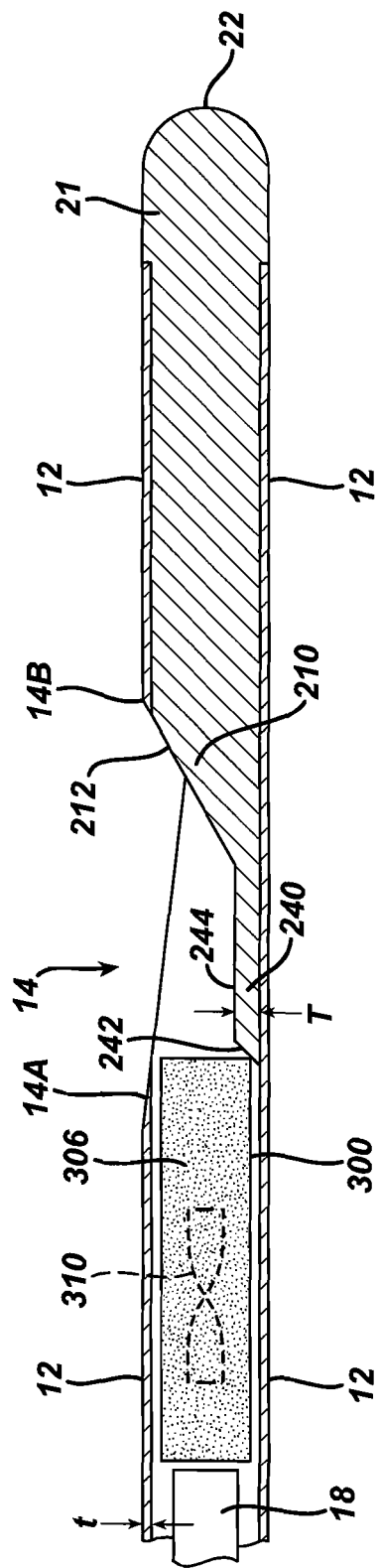
FIG. 2 depicts a cross-sectional view of a distal portion of a marker delivery device according to the present invention.

FIG. 2 depicts a cross-sectional view of a distal portion of the marker delivery device 10 according to one embodiment of the present invention. FIG. 2 shows a biopsy marker 300 disposed in the internal lumen 15 of the cannula 12. The marker 300 can comprise a biodegradable or otherwise resorbable body 306, such as a generally cylindrically shaped body of collagen, and a metallic, generally radiopaque marker element 310 (shown in phantom) disposed within or otherwise carried by the body 306.

The cannula 12 can be formed of any suitable metallic or non-metallic material. In one embodiment, the cannula 12 is formed of a thin walled hollow tube formed of a suitable medical grade plastic or polymer. One suitable material is a thermoplastic elastomer, such as Polyether block amide (PEBA), such as is known under the tradename PEBAX. The cannula 12 can be formed of PEBAX, and can be substantially transparent to visible light and X-ray.

The side opening 14 can be formed by cutting away a portion of the wall of cannula 12. The side opening 14 communicates with an internal lumen 15 of the cannula. The side opening 14 can extend axially (in a direction parallel to the axis of the lumen 15) from a proximal opening end 14A to a distal opening end 14B, as illustrated in FIG. 2.

The distal tip 22 extending from the distal end of cannula 12 can be rounded as shown in FIG. 2. Referring to FIG. 2, a marker delivery device of the present invention can have the distal end of the cannula 12 closed by a unitary endpiece 21 formed in place in the distal end of the cannula 12, with a part of the endpiece 21 extending into the internal lumen 15 of the cannula. The distal endpiece 21 can be a molded or cast component, and can provide an integrally formed combination of the tip 22, a ramp 210 having a ramp surface 212, and a marker engaging element 240. The ramp surface 212 aids in directing the marker 300 from the internal lumen 15 through side opening 14. The marker engaging element 240 helps to retain the marker 300 in the internal lumen 15 until the user intends to deploy the marker.

The marker engaging element 240 is disposed within the internal lumen 15, and at least a portion of the marker engaging element is disposed distally of the proximal end 14A of side opening 14. The marker engaging element 240 can extend along a portion of the floor of the cannula 15 under the opening 14, and the marker engaging element 240 can be positioned to reinforce the portion of the cannula in which the opening 14 is formed. For instance, by positioning the marker engaging element 240 underneath the opening 14, as shown in FIG. 2, the element 240 can help to stiffen the cannula 12 in the region where wall of the cannula 12 is cut to form the opening 14.

In the embodiment shown in FIG. 2, the marker engaging element 240 extends from the proximal most portion of ramp surface 212, and does not extend proximally of the side opening 14, though in other embodiments, a portion of the element 240 could extend proximally of the opening 14.

In the embodiment shown in FIG. 2, marker engaging element 240 is in the form of a step having a generally uniform thickness T along the element's axial length, except that the element has a tapered proximal end 242. The tapered proximal end 242 can form an included angle with the longitudinal axis of the lumen 15 (included angle with a horizontal line in FIG. 2) of about 45 degrees, while the ramp surface 212 can form an included angle with the longitudinal axis of about 30 degrees.

The thickness T can be greater than the wall thickness t of the cannula 12, and in one embodiment T is at least about twice the thickness t. In one embodiment, the thickness T can be between about 0.018 inch to about 0.040 inch, and the wall thickness t can be between about 0.005 inch to about 0.008 inch. The internal diameter of lumen 15 can be about 0.120 inch.

In the embodiment of FIG. 2, the upwardly facing surface 244 (surface facing the opening 14) marker engaging element 240 extends distally to contact the ramp surface 212, so that there is not a space or gap between the surface 244 and the ramp surface 212. Such an arrangement is advantageous to reduce the possibility that the marker 300, upon moving past the marker engaging element, will become lodged between the marker engagement element and the ramp.

According to one embodiment of the invention, the marker engaging element 240, ramp 210, and/or the tip 22 can be formed of, or include, a material that is relatively more radiopaque than the wall of the cannula 12.

For instance, where the element 240, ramp 210, and tip 22 are formed as an integral endpiece 21, the endpiece 21 can include a radiopaque additive, such as barium sulfate. For instance, the endpiece 21 can be a component molded of PEBAX, with about 20 percent by weight barium sulfate added to the molten PEBAX mold composition.

The relatively more radiopaque marker engaging element 240, ramp 210, and tip 22 can be useful in distinguishing the position of those components using radiographic imaging. Also, where the ramp and/or step of engaging element are positioned in association with the opening 14, the addition of a radiopaque material can help identify the position of the opening, and the position of the marker 300 relative to the opening before, during, or after deployment of the marker.

Only one marker is shown disposed in lumen 15 in the figures. However, it will be understood that multiple markers can be disposed in marker delivery device 10, such as in an end to end configuration. The markers can have the same size and shape, or alternatively have different sizes and/or shapes.

The cannula 15 can be generally transparent to visible light and x-ray, and the endpiece 21 can be generally opaque to visible light and x-ray. If desired, the endpiece 21 can be colored with a dye or other suitable colorant in the liquid mold composition. For example, it may be desirable to have different size markers (e.g. length and/or diameter) for different biopsy procedures. For instance, it may be desirable to provide a larger marker if a relatively large biopsy sample is taken, and a smaller marker if a relatively small biopsy sample is taken. The endpiece 21 can be colored using one of multiple colors to indicate the size of the marker disposed in the cannula. For instance, if three marker sizes are provided, the endpiece 21 can be colored one of three colors to identify which of the marker sizes are disposed in the cannula of a particular marker device. The endpiece 21 can also be colored to indicate a particular size (diameter or length) biopsy needle with which the marker delivery device is to be used. Additionally, multiple marker delivery devices could be packaged in kit form, with the kit including marker delivery devices having different size markers and correspondingly colored endpieces.

Figure 3:
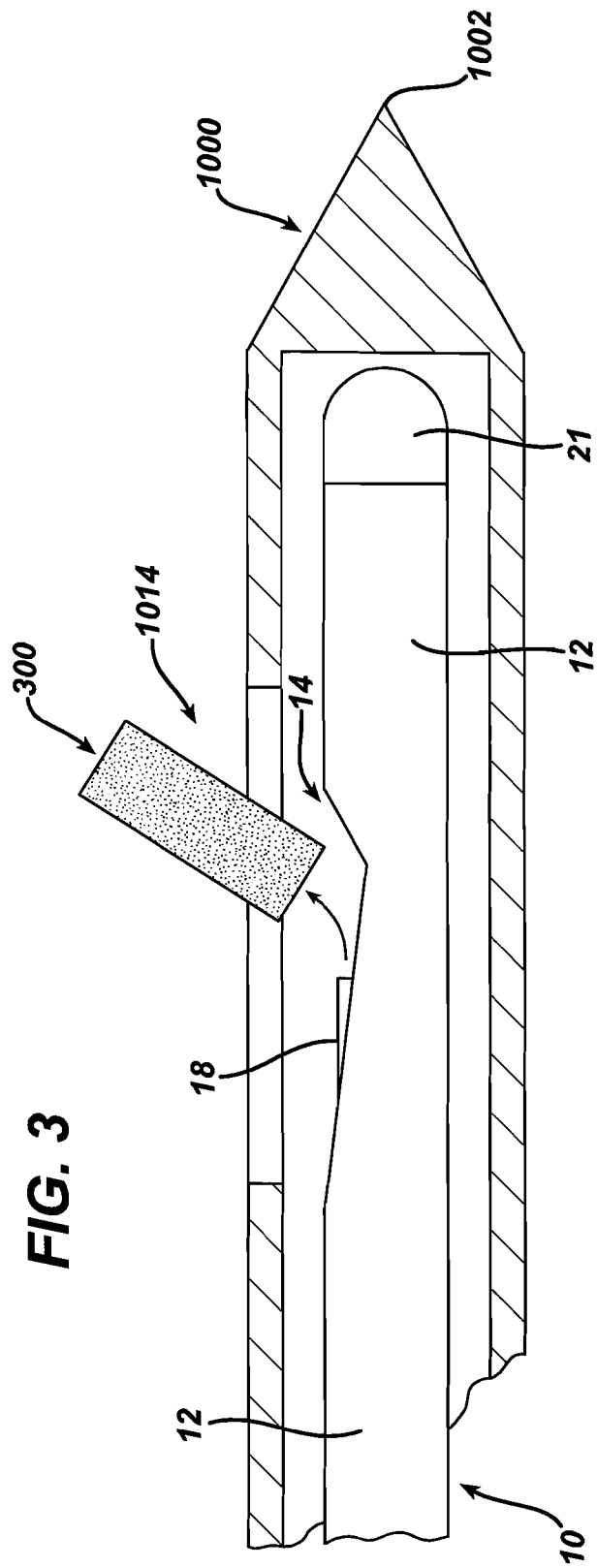
FIG. 3 depicts a marker being deployed from a deployer and through a lateral tissue receiving port in a biopsy needle to mark a biopsy site.

Referring to FIG. 3, the marker delivery device 10 may be used to deploy a marker to mark a particular location within a patient. In FIG. 3, a cannular biopsy needle 1000 is shown. The needle 1000 is shown having a closed distal end with piercing tip 1002, and a lateral tissue receiving aperture 1014. Marker deployer 10 may be introduced to a biopsy site through biopsy needle 1000, which can be the same needle used to collect a tissue sample from the biopsy site. The biopsy needle 1000 can be of the type used with single insertion, multiple sample vacuum assisted biopsy devices. Several such biopsy devices are disclosed in the various patents and patent applications that have been referred to and incorporated by reference herein, though other biopsy devices may be used.

FIG. 3 shows the distal end of a marker deployer 10 disposed within the needle 1000. The needle 1000 can be positioned in tissue, and a biopsy sample can be obtained through opening 1014, thereby providing a biopsy cavity adjacent opening 1014. Then, after the tissue sample has been obtained and transferred proximally through the needle, and without removing the needle 1000 from the patient's tissue, the deployer 10 can be inserted into a proximal opening in the needle 1000. In FIG. 3, the needle 1000 and deployer 10 are positioned such that opening 14 of cannula 12 and opening 1014 of needle 1000 are substantially aligned axially and circumferentially. Then, with the deployer and needle so positioned at the biopsy site, the push rod 18 can be advanced to deploy the marker up the ramp surface 212, through the opening 14, and then through opening 1014, into the biopsy cavity.

Figure 4:
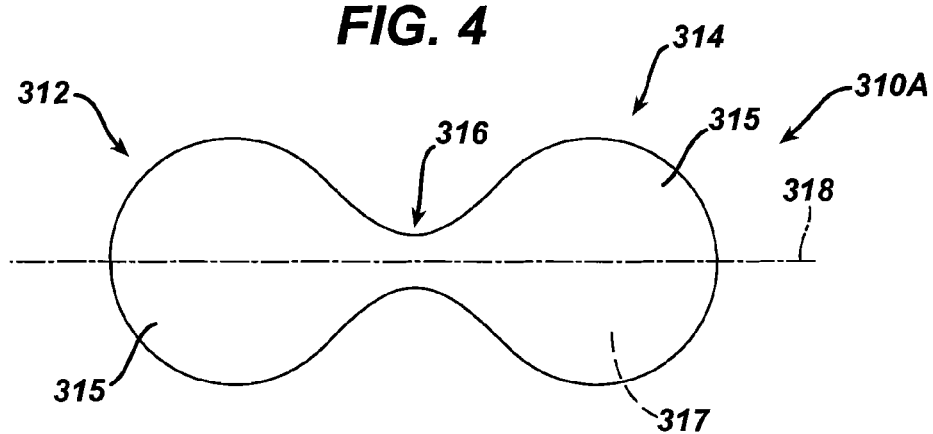
FIG. 4 depicts a generally planar piece of titanium having two relatively large lobes or ends separated by a narrow portion, which piece can be used to form a radiopaque marker element.
Figure 5:
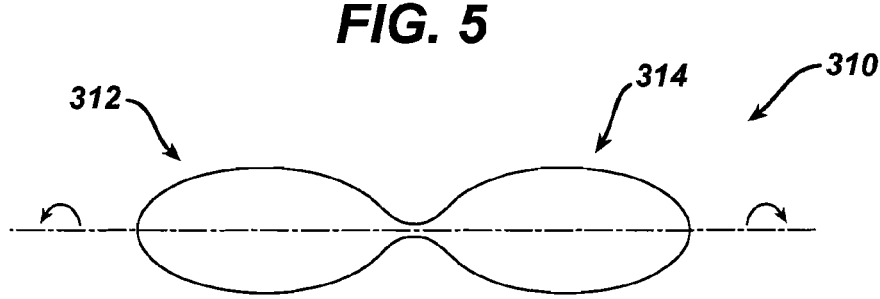
FIG. 5. depicts forming the planar piece of FIG. 4 to provide a three dimensional marker element, such as by twisting the two lobes in opposite directions as indicated by the arrows in FIG. 5.
Figure 6:
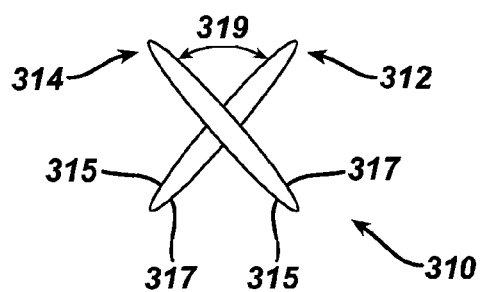
FIG. 6 depicts an end view of the marker element of FIG. 5, the marker element having a generally x-shaped configuration when viewed on end in FIG. 6.

FIGS. 4-6 provide description of a radiopaque marker element that can be used in connection with the marker delivery device 10. FIG. 4 illustrates a generally planar blank 310A of a radiopaque material, such as titanium, which can be cut or otherwise formed to have a first relatively large portion 312, a second relatively large portion 314, and a relatively narrow portion 316 connecting the first and second portions 312 and 314. The blank 310A can have a first side 315 and a second side 317.

The portions 312 and 314 are shown to be generally circular lobes, but other shapes, such as square, rectangular, triangular, oval could also be employed. To form a three dimensional marker element 310 (such as can be positioned within the bioresorbable body 306 shown in FIG. 2), the two lobes 312 and 314 can be twisted in opposite directions about axis 318, as indicated by arrows in FIG. 5. The two lobes 312 and 314 can be twisted such that the angle 319 between them (as viewed in FIG. 6) is between about 45 degrees and about 135 degrees. The resulting three dimensional radiopaque marker element 310 will have a generally x-shaped configuration when viewed on end, as shown in FIG. 6. Because the generally planar portions are 312 and 314 are twisted out of plane relative to each other, they can be more easily seen from various directions (e.g. top, bottom, side, end on) under various imaging methods, including x-ray. The three dimensional marker element 310 shown in FIGS. 5 and 6 can then be inserted into the bioresorbable body 306 (FIG. 2), or otherwise carried by the body 306, to provide a marker 300 having a resorbable body and a radiopaque marker element.

Figure 7:
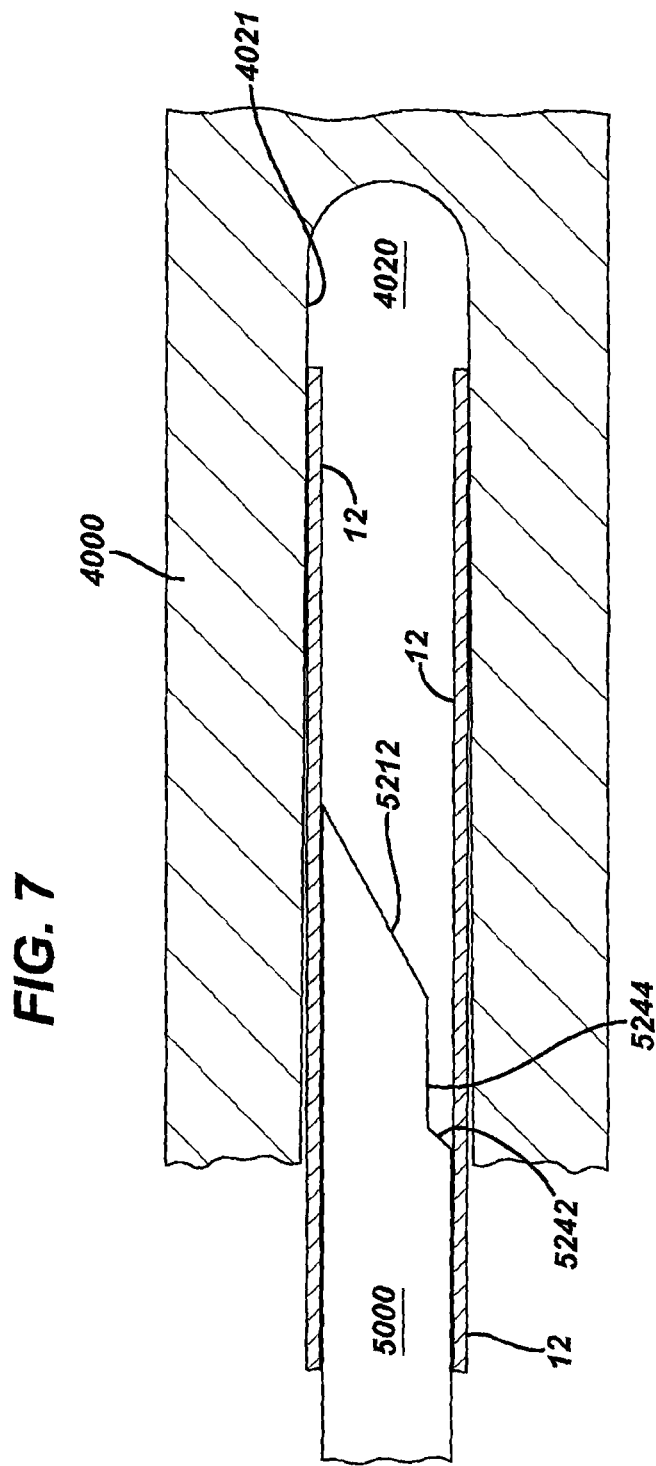
FIG. 7 illustrates an assembly for use in injection molding a unitary endpiece in the distal open end of a cannula to form the distal tip, ramp, and marker engaging element of a marker delivery device according to an embodiment of the present invention.

FIG. 7 illustrates an assembly which can be used to injection mold the unitary endpiece 21 in the distal end of cannula 12. The assembly can include a mold portion 4000 having a mold cavity 4020, including a rounded surface 4021 (corresponding to the rounded, generally hemispherical tip 21 of FIG. 2. The cannula 12 can be positioned in the cavity 4020 as shown in FIG. 7. A molding core component 5000, having generally cylindrical outer surface, can be positioned within the internal lumen of cannula 12, as shown in FIG. 7. The component 5000 can have end surfaces 5212, 5244, and 5242 corresponding to the ramp surface 212, the step surface 244, and the tapered end surface 242, respectively. A molten composition comprising the PEBAX and a radiopaque additive can then be injected into the cavity 4020, such that the endpiece 21 is formed in place in the distal opening of cannula 12.

Embodiments of the devices disclosed herein are generally designed to be disposed of after a single use, but could be designed to be used multiple times. After forming the marker, and inserting the marker into the deployer, the biopsy device can be sterilized. The device can be placed in a package, such as plastic or TYVEK bag.

The packaged biopsy device may then be placed in a field of radiation such as gamma radiation, x-rays, or high-energy electrons to sterilize the device and packaging. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed:

1. A biopsy marker delivery device comprising:
    a cannula having an internal lumen extending from a proximal end of the cannula to the distal end of the cannula, and a marker exit formed in a sidewall of the cannula proximal to the distal end of the cannula, wherein the cannula defines a longitudinal axis extending therethrough, wherein the distal end of the cannula defines an opening;
    a distal tip member closing the distal end of the cannula, wherein a proximal portion of the distal tip member extends proximally through the opening defined by the distal end of the cannula and along the interior of the sidewall of the cannula such that wherein the cannula extends distally beyond a proximal portion of the distal tip, wherein the proximal portion of the distal tip member is positioned within the cannula, wherein a distal portion of the distal tip member is positioned distal to the distal end of the cannula;
    a ramp positioned adjacent the marker exit, wherein the ramp defines a first included angle with the longitudinal axis, wherein the ramp forms a first planar surface, wherein the ramp is formed by the proximal portion of the distal tip member;
    a marker engaging element disposed within the internal lumen of the cannula, wherein at least a portion of the marker engaging element is disposed distally of a proximal end of the marker exit, wherein the marker engaging element comprises a tapered proximal end defining a second included angle with the longitudinal axis, wherein the tapered proximal end forms a second planar surface, wherein the marker engaging element extends proximally from the ramp, wherein the marker engaging element extends proximally along the sidewall of the cannula, wherein the marker engaging element has a thickness of at least twice the thickness of the sidewall of the cannula, wherein the marker engaging element is formed by the proximal portion of the distal tip member; and
    at least one marker disposed within the internal lumen of the cannula;
    wherein the cannula is transparent and the distal tip member is radiopaque.

2. The device of claim 1 wherein the ramp and marker engaging element comprise a unitary component.

3. The device of claim 1 wherein the distal tip member, ramp, and marker engaging element comprise a unitary component.

4. The device of claim 1 wherein the distal tip member, ramp, and marker engaging element comprise a unitary molded component.

5. The device of claim 1 wherein the cannula comprises a relatively flexible thin walled tube, and wherein the marker engaging element comprises a relatively stiff member disposed within the internal lumen.

6. The device of claim 1 wherein the marker engaging element comprises a step having a uniform thickness along at least a portion of its axial length.

7. The device of claim 1 wherein the distal tip member is relatively more radiopaque than the cannula.

8. The device of claim 7 wherein the distal tip member, ramp, and the marker engaging element are relatively more radiopaque than the cannula.

9. The device of claim 8 wherein the distal tip member, ramp, and marker engaging element comprise a radiopaque material.

10. The device of claim 9 wherein the distal tip member, ramp, and marker engaging element are a unitary molded component comprising barium sulfate.

11. The device of claim 1 wherein the marker engaging element extends along a floor of the internal lumen opposite of the marker exit.

12. The device of claim 1 wherein the marker engaging element is disposed in the cannula to reinforce the cannula.

13. A biopsy marker delivery device comprising:
 a cannula having a proximal end, a distal end, an internal lumen extending from the proximal end to the distal end, and a marker exit formed in the side wall of the cannula, said marker exit being defined by a distal edge and a proximal edge, wherein the distal end of the cannula forms a distal opening, wherein the cannula defines a longitudinal axis extending therethrough, wherein the distal edge and the proximal edge of the marker exit define a midpoint along the longitudinal axis positioned between the distal edge and the proximal edge;
 a unitary endpiece disposed in the distal end opening of the cannula, the unitary endpiece comprising:
  a distal tip, wherein the cannula extends distally beyond a proximal portion of the distal tip, wherein the proximal portion of the distal tip is positioned within the cannula such that the distal opening of the cannula circumferentially encloses the proximal portion of the distal tip, wherein a distal portion of the distal tip is positioned distal to the distal opening of the cannula,
  a ramp disposed proximally of the distal tip and having a ramp surface extending proximally from a distal end of the marker exit, wherein the ramp surface forms a planar surface, and
  a marker engaging element extending proximally from the ramp, wherein the marker engaging element comprises a tapered proximal end, wherein the tapered proximal end is positioned substantially proximal in relation to the midpoint, and
 at least one biopsy marker disposed within the internal lumen of the cannula, wherein the at least one marker comprises a bioabsorbable body and a radiopaque marker element, said at least one marker being disposed proximally of the marker engaging element,
 wherein the radiopaque marker element comprises a first end portion and a second end portion, wherein the first end portion and the second end portion are oriented in different planes;
 wherein the cannula is transparent and the endpiece is radiopaque.

14. A biopsy marker delivery device comprising:
 a cannula comprising a relatively flexible, thin walled tube having an open distal end, a proximal end, a lumen extending from the proximal end to the open distal end, and a marker exit formed in a side wall of the tube, the tube having a wall thickness, wherein the side wall of the tube defines a floor under the marker exit, wherein the floor has an interior surface on the inside of the tube and an exterior surface on the outside of the tube; and
 a unitary endpiece inserted in the open distal end of the tube such that the unitary endpiece is positioned to close the open distal end of the tube, the unitary endpiece comprising:
  a distal tip extending distally from the distal end of the tube,
  a ramp disposed proximally of the distal end of the tube, and
  a marker engaging element extending proximally from the ramp, wherein at least a portion of the marker engaging element extends along a portion of the floor of the tube under the marker exit formed in the tube such that the portion of the marker engaging element is positioned between the interior surface of the floor of the tube and the marker exit of the tube, wherein the marker engaging element has a thickness of at least twice the thickness of the tube; wherein the unitary endpiece is opaque relative to the thin walled tube; and
 at least one biopsy marker disposed in the lumen of the tube;
 wherein the tube is transparent and the endpiece comprises a radiopaque additive.

15. The biopsy marker delivery device of claim 14 wherein the endpiece comprises a radiopaque additive and a colorant.

16. The biopsy marker delivery device of claim 14 wherein the biopsy marker comprises bioabsorbable body and a radiopaque marker element disposed proximally of the marker engagement element.

17. The biopsy marker delivery device of claim 16 wherein the radiopaque marker element comprises a first relatively large end portion, a second relatively large end portion, and a third relatively narrow portion connecting the first and second end portions.

18. The biopsy marker delivery device of claim 16 wherein the radiopaque marker element comprises a first end portion, a second end portion, and wherein the first and second end portions are oriented in different planes.

* * * * *